(12) United States Patent
Chen

(10) Patent No.: US 8,158,159 B2
(45) Date of Patent: Apr. 17, 2012

(54) PHARMACEUTICAL FORMULATION FOR TREATING TINEA OF FEET AND HANDS AND PREPARATION THEREOF

(75) Inventor: Jinghua Chen, Shenzhen (CN)

(73) Assignee: Shen Zhen Bei Ke Lian Pharmaceutical Sci-Tech Co., Ltd., Shenzhen (CN)

( * ) Notice: Subject to any disclaimer, the term of this patent is extended or adjusted under 35 U.S.C. 154(b) by 443 days.

(21) Appl. No.: 12/298,961

(22) PCT Filed: Feb. 12, 2007

(86) PCT No.: PCT/CN2007/000485
§ 371 (c)(1),
(2), (4) Date: Oct. 29, 2008

(87) PCT Pub. No.: WO2007/124642
PCT Pub. Date: Nov. 8, 2007

(65) Prior Publication Data
US 2009/0130231 A1    May 21, 2009

(30) Foreign Application Priority Data

Apr. 29, 2006 (CN) .......................... 2006 1 0060468

(51) Int. Cl.
*A61K 33/06* (2006.01)
*A61K 31/045* (2006.01)
*A61K 36/483* (2006.01)
*A61P 17/00* (2006.01)
*A61P 17/02* (2006.01)
*A61P 31/10* (2006.01)

(52) U.S. Cl. ........ 424/682; 424/698; 424/769; 424/777; 514/729; 514/858

(58) Field of Classification Search .................. 424/698, 424/777, 682, 769; 514/729, 858
See application file for complete search history.

(56) References Cited

U.S. PATENT DOCUMENTS
2005/0158403 A1 * 7/2005 Lee .............................. 424/725

FOREIGN PATENT DOCUMENTS
| CN | 1140606 | | 1/1997 |
| CN | 1357348 | | 7/2002 |
| CN | 1751702 | * | 3/2006 |

OTHER PUBLICATIONS

HCAPLUS Abstract 2006:329189 (abstracting CN 1751702, Mar. 2006).*
HCAPLUS Abstract 2005:295821 (abstracting CN 1457814, Nov. 2003).*
HCAPLUS Abstract 2005:1513476 (abstracting CN 1513476, Jul. 2004).*
File Registry entry for "Alumen," STN Online, accessed on Sep. 22, 2010.*
Vargel, C. et al. Corrosion of Aluminum, Part A Aluminum and its alloys, pp. 3-5 (2004).*
International Search Report issued for International Application No. PCT/CN2007/000485 and mailed Jun. 14, 2007.

* cited by examiner

*Primary Examiner* — John Pak
(74) *Attorney, Agent, or Firm* — Hamre, Schumann, Mueller & Larson, P.C.

(57) ABSTRACT

A pharmaceutical formulation for treating tinea of feet and hands is disclosed, which is composed of Fructus Gleditsia, Alumen and Borneol. Also disclosed is a cream preparative method of the pharmaceutical formulation, which comprises Fructus Gleditsia is decocted with water, and the decocted liquid is dried under decompression into powder, which is formulated to a cream together with the powders of Alumen and Borneol as well as the respective excipients.

4 Claims, No Drawings

PHARMACEUTICAL FORMULATION FOR TREATING TINEA OF FEET AND HANDS AND PREPARATION THEREOF

BACKGROUND

Tinea of feet and hands is a kind of fungal dermatopathy on the feet and hands, which is superficial skin infection mainly caused by *Epidermophyton, Microsporum* and *Trichophyton*. The incidence of tinea pedis is higher than that of tinea manum, which is common skin disease. The incidence of tinea pedis could nearly accounts for 80% in tinea disease. The incidence of tinea disease in south China is higher that in the north due to wet climate. The incidence in workers wearing rubber shoes in some places is as high as 80%. The national average incidence in high-incidence area of tinea of feet and hands is as high as 30%, and the age of affected population ranged from 25 to 45. The recurrent attacks of this disease disturbs people's lives in a long term and bring tremendous mental burden to patients.

Current pharmaceuticals for treatment of tinea of hands and feet can be classified as western medicine preparations and traditional Chinese medicine preparations. Among western medicine preparations, the representative medicine are Miconazole, Lamisil and Fluconazole. But most western medicine preparations possess certain hepatotoxicity and nephrotoxicity, which will be harmful to liver and kidney functions with long-term application. For example, due to serious hepatotoxicity and nephrotoxicity, the clinical application of Fluconazole is gradually decreasing. Such new-generation of western medicine preparations as Miconazole, although it has relatively mild toxicity and fewer adverse reactions, long-term application will still bring about certain toxicity and adverse reactions and high relapse rate as well as high reoccurrence rate.

Modern pharmacology study methods have discovered that many traditional Chinese medicines, such as *Sophora flavescens Ait, Fructus Kochiae, Densefruit Pittany* Root-bark and *Cortex Phellodendri*, have significant inhibitory effects on various dermatophyte. According to traditional Chinese medicine theories and treatment experiences summarized from long-term clinical application, many traditional Chinese medicine preparations for treating tinea of feet and hands have been developed, which were made into many effective dosage forms Chinese patent medicine such as tincture, liquid medicine and cream with advanced modern extraction techniques.

Current traditional Chinese medicine preparations for treatment of tinea of feet and hands include compound Pseudolaric tincture, Gehong Medical liquid for the tinea pedis and elixir water of tinea. But the efficacy of these preparations is not satisfactory due to simple preparation techniques.

Along with increased attention has been paid onto the modernization study of traditional Chinese medicine, and people have raised their healthcare awareness and pursued natural medicines, green medicines. The toxic and adverse effects of western medicine have been gradually discovered. Now there are increasing traditional Chinese medicine varieties under researching, however, few traditional Chinese medicine preparations can meet the requirement of satisfactory treatment in tinea of feet and hands.

At present, the biggest problem in therapeutic drugs for treatment of tinea of feet and hands is high relapse rate of the disease, which is chronic disease for most patients and can't be solved by all existing medicines. The long application period of current medicines influenced therapeutic effects.

PURPOSE OF INVENTION

The purpose of the present invention is to provide a kind of traditional Chinese medicine preparation for the treatment of tinea of feet and hands to overcome the shortcomings of traditional Chinese medicine preparation for the treatment of tinea of feet and hands, such as high relapse rate, long application period and dissatisfied therapeutic efficacy.

Another purpose of the present invention is to provide a preparative method of traditional Chinese medicine cream preparation for the treatment of tinea of feet and hands.

Based on the knowledge and therapeutic principle of the pathological mechanism of tinea of feet and hands in traditional Chinese medicine, the solution of the present invention referred to the achievements of modern pharmacological study and selected a combination of Fructus Gleditsia, Borneol and Alumen from the treasury of traditional Chinese medicine. The Alumen is an astringent and have the function of depriving the evil wetness, Borneol have the function of heat-clearing, detoxicating, and odynolysis, and the Fructus Gleditsia have the function of dampness elimination and suppressing fungi. The interactive combination of the three traditional Chinese medicines can play effects of clearing away heat evil and promoting dieresis, detoxicating, suppressing fungi, promoting tissue regeneration and relieving itching. It can be indicated for all tinea diseases, especially for tinea of feet and hands and those diseases considered as syndrome of excessive wet heat spreading according to differentiation of symptoms and signs in traditional Chinese medicine. After long-term application of this pharmaceutical formulation of traditional Chinese medicine in the treatment of tinea of feet and hands, it has been indicated for syndrome of excessive wet heat spreading by symptomatic treatment, it can achieve high curative rate and low relapse.

SUMMARY

A pharmaceutical formulation for the treatment of tinea of feet and hands is composed of preparations as follows (by weight):

Fructus Gleditsia 55%-65%, Borneol 8%-15%, Alumen 15%-30%.

The ratios adopted in an embodiment of the present invention:

Fructus Gleditsia 62.5%, Borneol 12.5%, Alumen 25%.

In above prescriptions, Borneol is one kind of products made from resin of Dipterocaraceae plants. The crystallized products, which called Borneolum Blumeae(Ai pian) are made from cooled distillation of Compositae plant Blumea balsnmifera, and artificial synthetic products made from oil of turpentine (called as Synthetic Borneol).

Nature, flavour and meridian belongingness: pungent, bitter, mild cold, belongs to meridian of heart, spleen and lung.

Efficacy: analepsia and waking up a patient from unconsciousness, heat-clearing and odynolysis.

Clinical Application:

1. The efficacy of Borneol in the treatment of syncope or faints is similar with that of musk but with milder effects, and it can be used in combination with musk for the treatment of syncope or faints. It has been mainly clinically used to treat syncope in thermy and heat diseases, as well as internal blockade symptoms such as stroke, phlegm syncope, syncope resulting from disorder of vital energy, attacked by pestilent factors, sudden fainting and so on.
2. Borneol is also indicated in the treatment of pyocutaneous disease, scabie and tinea, canker sore, throat sore and eye diseases.

Prescription name: Borneol, Plum Borneol, borneo camphor, fragrant brain, slice brain (named after the original plants *Dryobalanops aromatica* tree).

Fructus Gleditsia (annotation: Fructus Gleditsia for medicine use) is the fruit of Gleditsia sinensis Lam.

Nature, flavour and meridian belongingness: pungent, warm, less toxicity, belongs to lung and large intestine meridian.

Efficacy: eliminating phlegm and waking up a patient from unconsciousness.

Clinical Application:
1. Fructus Gleditsia can be indicated for cases with cold wetness, and stagnation, chest distress and cough with asthma, excessive phlegm without proper expectoration. Fructus Gleditsia has a strong function of eliminating phlegm, which can be used for the treatment of patients with damp-phlegm, stagnation without proper expectoration. This product can be dried into powder and prepared into boiled soup with red date for single use or combined with *Rhizoma Pinelliae* and semen raphani.
2. Fructus Gleditsia can be indicated for diseases and symptoms of faint, epilepsy, excessive phlegm, and sense stagnation. Fructus Gleditsia is pungent and thus it have functions to waking up a patient from unconsciousness. It can be used for the treatment of cases with symptoms of faint and stagnation, and it can also be combined with powders of *Arisaema erubescens, Rhizoma Pinelliae, Herba Asari*, Wild Mint Herb and realgar to be administered nasally to make the cases sneeze. Fructus Gleditsia can be applied onto edemas (without ulcer) and have edema elimination effects.

Alumen

Clinical Application:
1. Clearing heat and eliminating phlegm per os: it can be used in the treatment of epilepsy, always combined with Yu Jin Ming Bai Jin pill. Take 1-3 gram per os.
2. Depriving the evil wetness and suppressing fungi with external application: it can be used in the treatment of scabie, tinea and itching. Apply suitable amount of it for external application, take its powder onto affected area or wash with combination of water.

The pharmaceutical formulation in the present invention can be prepared into above mentioned pharmaceutical formulations.

The preparative methods of cream preparation of this medicine for the treatment of tinea of feet and hands are as follows:
1. Take 200 gram of Fructus Gleditsia powder into six-fold (by weight) water and decoct it for 1.5 hour, and then collect the decocted liquid;
2. Add five-fold (by weight) water into Fructus Gleditsia powder for two times, and decoct it for 1.5 hour, and then collect the decocted liquid;
3. Put together the decocted solution and distilled water solution obtained from Step 1 and 2, filtration, and then the filtrate is concentrated as liquid with relative density of 1.10-1.15 (at 80° C.) under decompression. Then add ethanol to make the concentration of alcohol reach 60%, stir it adequately and make it still for 24 hours. Then perform filtration, recover ethanol and then the filtration is concentrated into liquid with relative density of 1.30-1.35 (at 80° C.) under decompression. Then the liquid is dried under decompression into powder for the preparation of powder preparation;
4. Make 80 gram of Alumen and 40 gram of Borneol into powder preparation for further preparation;
5. Heat the water phase composed of 4.5 ml TEA, 25 gram of Tween-80, 100 ml glycerol and water and oil phase composed of 50 gram of stearic acid, 35 gram of liquid paraffin, 30 grams of Vaseline and 35 gram of glyceryl monostearate to the temperature of 80° C. and keep it at this temperature. Then put the oil phase into water phase and continuously stir and keep it at 80° C. for 15 minutes. Cool it down to the temperature of 40° C., add the powder preparation prepared in Step 3 and 4, stir it to room temperature and then 1000 gram of the final product has been prepared.

The Main Pharmacodynamic Action of the Pharmaceutics in the Present Invention:
1. In vitro bacteriostasis test (plate method) showed that the pharmaceutics in the present invention has significant inhibitory effects on the growth of *Monilia albican, Staphylococcus aureus, Hemolytic streptococcus, Pseudomonas aeruginosa* and *E. coli*.
2. Anti-inflammation effects: local administration of this pharmaceutics can reduce the degree of rat inflammation edema in feet caused by carrageenan, and significantly inhibit the degree of mouse inflammation edema in ears caused by xylene, which shows certain ameliorating effect on acute exudative inflammation.
3. Anti-itching effects: research on anti-itching effects of the pharmaceutics in the present invention has shown that local administration of this cream can significantly reduce the degree of itching in guinea pigs caused by Histamine diphosphate and elevate the itching threshold.
4. Analgesic effects: this cream can elevate the pain threshold of test animal (heat board method), which indicates that it has certain analgesic effect.

Drug Toxicological Study of the Present Invention:

Animal Acute Study

To investigate the safety effects of high-dose administration of the pharmaceutical cream preparation of the present invention on experimental animal, then observation was conducted according to the requirements of toxicological experiment observation.

In this research, the toxic reaction in intact skin and damaged skin caused by the drug of this invention have been observed, and the results showed that there is no toxic reaction in intact skin and damaged skin during continuous observation for 24 hours, 48 hours, 72 hours and 7 days at the doses of 200 ml and 100 ml of the pharmaceutics of the present invention in the test rabbits. This indicates that the pharmaceutics in the present invention is low toxic and safety in skin local administration.

Long-Term Toxicity Test 24 white adult healthy rabbits were used in this test, through repeated skin administration, the toxic reactions of intact skin and damaged skin were observed respectively. Method: once application a day, Continuous administration for 12 weeks and reversible observation for 2 weeks, The results showed that after the end of administration stage and reversible observation stage after drug discontinuation, the blood samples were collected for blood routine test and blood biochemistry test. There is no significant difference compared with those results of control group, which indicates that this preparation doesn't have any adverse effects on the blood, liver function or kidney function in test animals. There is no pathological changes related to toxicity in gross appearance or microscopic detection. There is no secondary toxic reaction after the drug discontinuation, which suggested that the local administration of this preparation is safety.

Skin Irritation Experiments

White guinea pigs were chosen for this experiment, animal skin irritation reactions and other adverse reactions in given period have been observed on test animals that have had contacted the pharmaceutics in the present invention.

To evaluate the irritation reaction according to skin irritation experiment scoring criteria, the results showed that there is no irritation reactions such as erythema or edema when observed closely for 24 and 48 hours after skin administration of test animals in two test regions of hand, which indicated that this preparation has no significant irritation effects on skin.

Skin Allergic Experiments

The results showed that the test animals are in good situation, no behavior abnormity, asthma, shock or other allergic reactions have been found and no irritation reactions such as erythema or edema in test regions of hand. The hypersensitivity reaction level is 0, and allergic ratio is 0, which indicated that there is no allergic effect of the cream pharmaceutical preparation in animals that have contacted it.

Phase I Clinical Study and Statistic Data of the Pharmaceutics in the Present Invention:

Purpose: to observe the efficacy of the pharmaceutical cream preparation of the present invention on cases with tinea of feet and hands (damp and heat type) and the clinical administration safety.

Diagnosis and Inclusion Crisis of Patients

Totaled 137 patients with tinea of feet and hands have been observed, who diagnosed as tinea of feet and hands (superficial fungus) after clinical examination conducted by physicians according to western medicine and damp heat symptoms in traditional Chinese medicine (itching and pain symptoms in the hands and feet, pinpoint-size semi-opaque blisters with firm walls in the affected positions which contains liquid or can lead to erythema and papule, red and greasy body of the tongue, rapid and slippery pulse).

Exclusion Standards

Following cases are excluded from this study: patients with combined cardiocerebralvascular diseases, serious primary diseases in liver, kidney and hematopoietic system, mental problems, and patients with allergic dermatosis complicated with eczema.

Medicines and Methods

This pharmaceutical cream preparation of the present invention: provided by Shen Zhen Bei Ke Lian Pharmaceutical Sci-tech Co. Ltd 20 g/tube.

Experiment methods: pharmaceutical cream preparation of the invention for external use, apply this onto the affected area, once in the morning and evening respectively in three weeks' course of treatment.

Observed Index:

General safety index, blood and urine routine test, liver function test, symptom scoring evaluation, microscopic detection of fungus, weekly follow-up and twice index detection before and after the treatment.

Efficacy Determination Criteria:

According to the efficacy determination criteria in guideline principle of new drug clinical trial of traditional Chinese medicine to judge and evaluate its efficacy:

Full recovery: skin damage and itching symptoms disappeared completely and microscopic observation of fungus shows negative results;

Marked effective: skin damage and most itching symptoms disappeared, total scoring of chief symptoms decreased (no less than 70%), and microscopic observation of fungus is negative or few thallospores;

Effective cases: skin damage and most itching symptoms disappeared, total scoring of chief symptoms decreased (30%-69%), and microscopic observation of fungus only found few deformed spores;

The reduction rate of total scoring of chief symptoms= (Pretherapy total scoring subtracts post-treatment total scoring)/pretherapy total scoring×100%.

No effect: compared with pretherapy symptoms, there is no improvement in all aspects and the reduction ratio of total scoring of chief symptoms is less than 30%.

Mycological therapeutic effect: microscopic detection(−) signifies clearance, microscopic detection(+)preclude clearance.

Ratio of recovery and effectiveness=(full recovery+effectiveness)/total cases×100%.

Results

After 3-week application of treating with this cream preparation of the present invention, index test was conducted. After statistic analysis, totaled 137 cases have been observed in Phase I clinical trial composed of 128 cases with tinea pedis and feet and 9 cases with tinea manus, including 62 full recovered cases after treatment, 38 cases with marked effective and 25 effective cases. Full recovery-effectiveness rate was 72.99%, the clearance rate of fungus was 81.02%, including 111 negative cases and 26 positive cases. The observed relapse rate in the follow-up after six weeks was 4.58%, see following table.

TABLE 1

Analysis of clinical efficacy

| | Case number | Full recovery | Marked effective | Effective | No effect | Full recovery-effectiveness rate | Total effective rate |
|---|---|---|---|---|---|---|---|
| $1^{st}$ week | 137 | 38 | 45 | 24 | 30 | 60.59% | 78.10% |
| $2^{nd}$ week | 137 | 50 | 43 | 18 | 26 | 67.88% | 81.02% |
| $3^{rd}$ week | 137 | 62 | 38 | 25 | 14 | 72.99% | 89.78% |

TABLE 2

Comparisons of its anti-fungus efficacy and 6-week reoccurrence rates

| Clearance rate in the third week | | | | Clinical relapse rate in sixth week | | | |
|---|---|---|---|---|---|---|---|
| Case number | Negative | Positive | Clearance rate | Case number | Recurrent | Non-recurrent | relapse rate |
| 137 | 111 | 26 | 81.02% | 137 | 6 | 131 | 4.58% |

No erythema, edema or allergic adverse reactions have been found in clinical trial, which indicates that the pharmaceutical formulation in the present invention is good in safety and tolerance as well as reliable efficacy.

What is claimed is:

1. A pharmaceutical formulation for the treatment of tinea of feet and hands, which is composed of preparations in following weight ratios:

Fructus Gleditsia 55%-65%, Borneol 8%-15%, Alumen 15%-30%.

2. The pharmaceutical formulation for the treatment of tinea of feet and hands according to claim 1, wherein the weight ratios are:

Fructus Gleditsia 62.5%, Borneol 12.5%, Alumen 25%.

3. The pharmaceutical formulation for the treatment of tinea of feet and hands according to claim 1, wherein the pharmaceutical formulation is prepared into an effective dosage form.

4. A cream preparation method of pharmaceutical formulation for the treatment of tinea of feet and hands, comprising steps of:
   (1) Providing 200 grams of Fructus Gleditsia powder into six-fold water by weight and decocting it for 1.5 hours to provide a first decocted liquid, and then collecting said first decocted liquid;
   (2) (a) Adding five-fold water by weight into said first decocted liquid, and decocting it for 1.5 hours to provide a second decocted liquid, and collecting said second decocted liquid;
   (2) (b) Adding five-fold water by weight into said second decocted liquid, and decocting it for 1.5 hours to provide a third decocted liquid, and then collecting said third decocted liquid;
   (3) (a) Concentrating the third decocted liquid under reduced pressure into a liquid with relative density of 1.10-1.15 at 80° C. to provide a fourth decocted liquid;
   (3)(b) Adding sufficient amount of ethanol to said fourth decocted liquid to make the concentration of ethanol reach 60%, stirring adequately and then leaving it still for 24 hours to provide an ethanol-containing solution;
   (3)(c) Filtering said ethanol-containing solution, removing the ethanol from the solution, and then concentrating under reduced pressure into a liquid with relative density of 1.30-1.35 at 80° C., then drying the liquid under reduced pressure to provide a first powder;
   (4) Providing and mixing 80 gram of Alumen and 40 gram of Borneol to provide a second powder; and
   (5) Heating a water phase composed of 4.5 ml TEA, 25 grams of Tween-80, 100 ml glycerol and water and an oil phase composed of 50 gram of stearic acid, 35 grams of liquid paraffin, 30 grams of Vaseline and 35 grams of glyceryl monostearate to a temperature of 80° C. and keeping it at this temperature, then putting the oil phase into water phase and continuously stirring and keeping it at 80° C. for 15 minutes, cooling it down to the temperature of 40° C., adding said first powder and said second powder to provide a mixture, stirring said mixture to room temperature to obtain a pharmaceutical formulation for the treatment of tinea of feet and hands in cream preparation form.

* * * * *